United States Patent [19]
Colinas et al.

[11] Patent Number: 5,985,658
[45] Date of Patent: Nov. 16, 1999

[54] CALMODULIN-BASED CELL SEPARATION TECHNIQUE

[75] Inventors: Robert James Colinas; Anne Catherine Walsh, both of Cambridge; David A. Lawrence, Slingerlands, all of N.Y.

[73] Assignee: Health Research Incorporated, Rensselaer, N.Y.

[21] Appl. No.: 08/970,363

[22] Filed: Nov. 14, 1997

[51] Int. Cl.⁶ .............................. C12N 5/00; C12N 5/02; G01N 33/53; G01N 33/536
[52] U.S. Cl. ......................... 435/325; 435/378; 435/7.2; 436/536; 436/538; 436/540; 436/541
[58] Field of Search .................................... 436/536, 538, 436/540, 541; 435/325, 378, 7.2

[56] References Cited

U.S. PATENT DOCUMENTS

| | | |
|---|---|---|
| 4,812,401 | 3/1989 | Tarnowski et al. . |
| 5,136,095 | 8/1992 | Tarnowski et al. . |
| 5,182,262 | 1/1993 | Leto . |
| 5,304,487 | 4/1994 | Wilding et al. . |
| 5,370,993 | 12/1994 | Tarnowski et al. . |
| 5,405,743 | 4/1995 | Tarnowski et al. . |
| 5,518,882 | 5/1996 | Lund et al. .................................. 435/6 |
| 5,635,358 | 6/1997 | Wilding et al. . |
| 5,731,425 | 3/1998 | Brizzard et al. ........................ 536/23.1 |
| 5,773,224 | 6/1998 | Grahdics et al. ......................... 435/7.2 |

FOREIGN PATENT DOCUMENTS

| | | |
|---|---|---|
| 43 40 129 C1 | 10/1994 | Germany . |
| WO 94/20858 | 9/1994 | WIPO . |
| WO 95/24648 | 9/1995 | WIPO . |
| WO 97/00329 | 1/1997 | WIPO . |

OTHER PUBLICATIONS

O'Neil and DeGrado, TIBS 15:59–64 (1990).
Klee and Vanaman, Adv Prot Chem 35:213–321 (1982).
Billingsley et al., Proc Natl Acad Sci USA 82:7585–7589 (1985).
Hopp, T.P., et al., Bio/Technology, 6:1204–1210 (1988).
Nilsson, B., et al., EMBO J., 4:1075–1080 (1985).
Hellebust, H., et al., J. Bacteriol., 172:5030–5034 (1990).
Knappik, A., and Pluckthun, A., BioTechniques, 17:754–761 (1994).

*Primary Examiner*—Paula K. Hutzell
*Assistant Examiner*—Yvonne Eyler
*Attorney, Agent, or Firm*—Braman & Rogalskyj, LLP

[57] ABSTRACT

The invention provides a method for separating target cells from a plurality of cells which is based on a reversible high affinity interaction between two molecules. The method comprises: forming a target cell/cell binding reagent/first molecule/second molecule/solid support complex, wherein the cell binding reagent is specific for target cells present within a plurality of cells and wherein the first molecule reversibly binds to the second molecule; removing non-target cells of the plurality of cells not attached to the solid support; and reversing the first molecule binding to the second molecule, thereby releasing the target cells as separate cells from the plurality of cells.

13 Claims, 7 Drawing Sheets

FROM FIG. 13 →

FROM FIG. 14 →

FROM FIG. 15 →

Title: 5,985,658

CALMODULIN-BASED CELL SEPARATION TECHNIQUE

This invention was made with support under National Institutes of Health Grant No. ES05020.

FIELD OF THE INVENTION

The subject invention is directed generally to a cell separation technique, and more particularly to a cell separation technique based on a reversible high affinity interaction between two molecules.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

The isolation of a phenotypically unique subpopulation of cells from a heterogenous cell population based on differential expression of cell surface markers is an essential step in many medical and biological research investigations. In addition, several protocols for the treatment of hereditary or acquired diseases that depend on the efficient selection of subpopulations of cells either are currently being employed or are in clinical trials. For example, in bone marrow (BM) or peripheral blood stem cell transplantation, hematopoietic stem/progenitor cells (HPC) are being purified from harvested BM or leukophoresis products to eliminate contaminating tumor cells or potentially alloreactive T cells (reviewed in Gee 1994; Berenson et al. 1996). In addition, stem cell gene therapy protocols are under development that also rely on HPC selection (Kohn 1995). Thus, it is clear that cell separation technologies are important in basic biological and medical research and in clinical medicine and the importance of this technology is likely to grow in the future.

At present, the available cell separation media employ monoclonal antibodies (Mab) that bind to specific cell surface antigens and are linked to solid (Lebkowski et al. 1992; Bensinger et al. 1990) or magnetic (Egeland et al. 1993; Miltenyi et al. 1990) matrices through covalent means or via biotin/avidin or immunoglobulin/anti-immunoglobulin interactions. The cells are either used without detachment from the matrix or are released by mechanical agitation, enzymatic digestion or dissociation induced by binding of an anti-mouse Fab antibody (Shpall et al. 1994). The mechanical agitation and enzymatic methods for releasing bound cells can result in damage to the targeted cell population and are difficult to monitor. Accordingly, a cell separation methodology is still needed that can separate target cells with specificity and without damaging the target cells.

SUMMARY OF THE INVENTION

The subject invention addresses this need by providing a method for separating target cells from a plurality of cells which is based on a reversible high affinity interaction between two molecules. The method comprises: forming a target cell/cell binding reagent/first molecule/second molecule/solid support complex, wherein the cell binding reagent is specific for target cells present within a plurality of cells and wherein the first-molecule reversibly binds to the second molecule; removing non-target cells of the plurality of cells not attached to the solid support; and reversing the first molecule binding to the second molecule, thereby releasing the target cells as separate cells from the plurality of cells.

In a preferred embodiment, the cell selection system is based on the reversible interaction between calmodulin (CM) and a CM-binding peptide (CBP). CM is a ubiquitous 17 kDa cytosolic calcium ($Ca^{2+}$)-binding protein. Each CM molecule binds four $Ca^{2+}$ ions with association constants (K) of $10^{-6}$–$10^{-7}$M (Linse et al. 1991). When the $Ca^{2+}$-binding sites of CM are occupied, CM binds to a number of cellular proteins through high affinity (K=$10^{-8}$–$10^{-9}$M) interactions with a specific peptide sequence motif termed the CBP present in a number of cellular proteins (Klee and Vanaman 1982; O'Neil and DeGrado 1990). However, when $Ca^{2+}$ is removed or chelated away from CM, the affinity of CM for the CBP is greatly reduced and the CBP is released by CM. A schematic diagram of the CM/CBP-based cell selection system is shown in FIG. 1. In this embodiment, target cells, labeled with a primary antibody specific to a cell surface antigen (the cell binding reagent), are recognized by a secondary GAM-IgG (the anti-cell binding reagent molecule) conjugated to a CBP (the first molecule). In the presence of $Ca^{2+}$, the GAM-IgG-CBP is recognized by biotinylated CM (CM-Biotin) (the second molecule) and a streptavidin (SA)-solid support. Removal of $Ca^{2+}$ by a chelating agent such as EGTA (the third molecule) reduces the affinity of CM for the CBP and results in the release of the bound target cell. Furthermore, because the CBP-binding ability of CM can be regenerated by removal of the chelator and readdition of $Ca^{2+}$, a CM-CBP-based cell separation system utilizing solid-phase CM has the potential for reusability. Furthermore, the CM/CBP-based cell separation system can be used in conjunction with other commercially available cell separation technologies, making it possible to purify a subpopulation of cells by sequential positive selection for multiple cell surface markers.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION OF THE INVENTION

Figure 1:
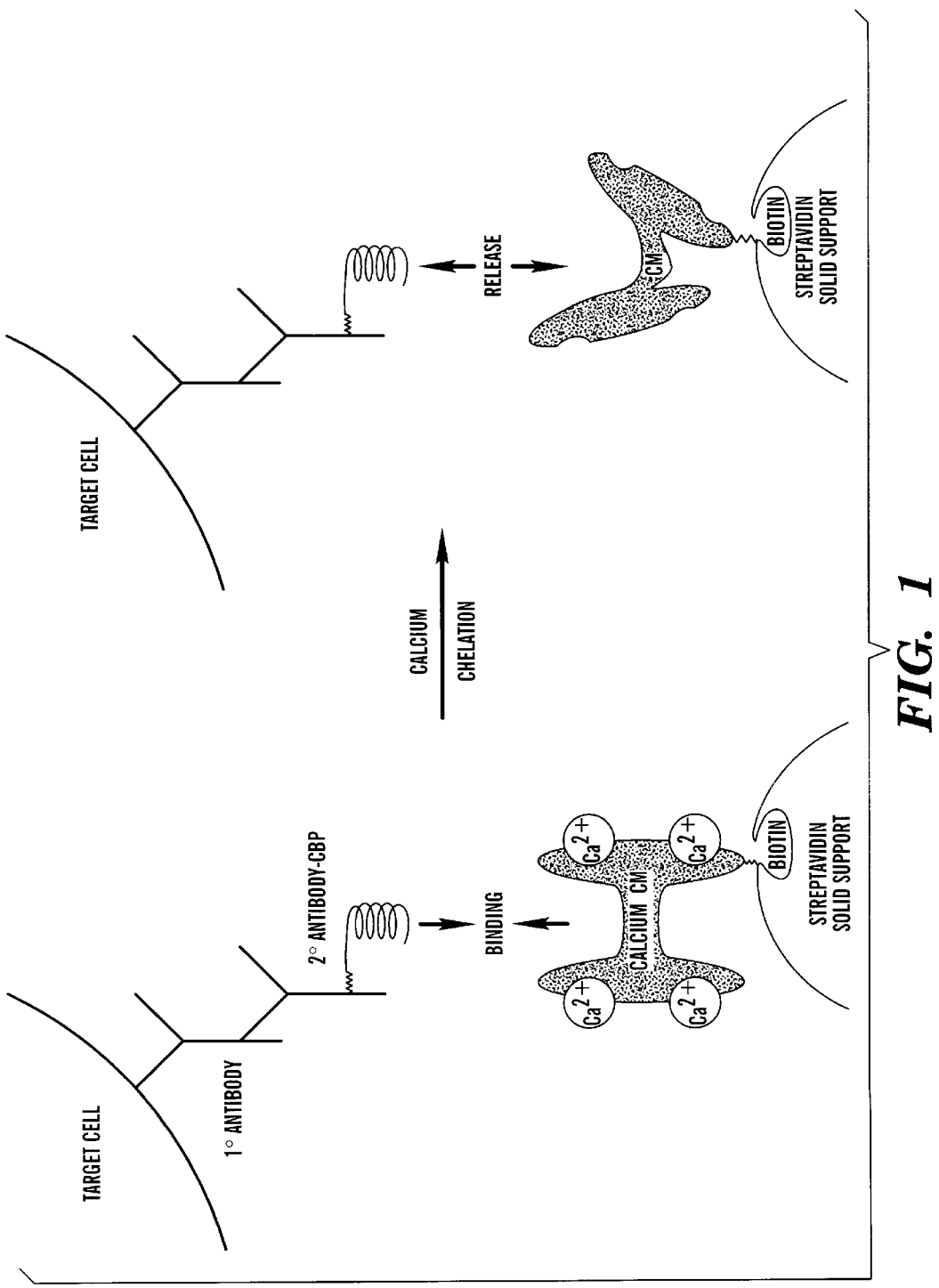
FIG. 1 is a schematic diagram of one embodiment of the subject invention, namely the cell separation system based on the reversible interaction of CM and CBP.

The subject invention provides a method for separating target cells from a plurality of cells which is based on a reversible high affinity interaction between two molecules. The method comprises: forming a target cell/cell binding reagent/first molecule/second molecule/solid support complex, wherein the cell binding reagent is specific for target cells present within a plurality of cells and wherein the first molecule reversibly binds to the second molecule; removing non-target cells of the plurality of cells not attached to the solid support; and reversing the first molecule binding to the second molecule, thereby releasing the target cells as separate cells from the plurality of cells.

The method of the subject invention is based on a reversible high affinity interaction between two molecules. One of the two molecules is attached to the target cell of interest, and the other of the two molecules is attached to a solid support. By exposing a plurality of cells (which include "labeled" target cells, e.g. labeled with one of the two molecules) to the solid support, the molecule attached to the target cells interacts with (e.g. binds to) the molecule attached to the solid support. The invention is based on this interaction being reversible. For example, in one presently preferred embodiment one of the first and second molecules is calmodulin and the other of the first and second molecules is a calmodulin binding peptide. The calmodulin can be attached to the solid support when the calmodulin binding peptide is attached to the target cell, or alternatively the calmodulin binding peptide can be attached to the solid support when the calmodulin is attached to the target cell. The interaction between calmodulin and the calmodulin binding peptide requires the presence of calcium. If calcium is not present, or if the calcium is chelated (for example, with EGTA), the two molecules do not bind to one another. Accordingly, and in accordance with the subject invention, in the presence of calcium the target cell will bind to the solid support, while the other cells in the plurality of cells being passed over the solid support will not bind. After non-bound cells are removed (for example, by washing with a buffer), the target cells can be released from the solid support by removing calcium. Calcium can be removed, in one embodiment, by chelating the calcium with EGTA. The target cells are then released from the solid support and can be collected as separated cells (separated from the plurality of cells).

Any pairs of molecules which reversibly interact and which can be attached to the target cell and the solid support can be used in the method of the subject invention. For example, a peptide termed "FLAG" has been identified which reversibly interacts with an anti-FLAG antibody (Hopp et al. 1988; Knappik and Pluckthun 1994). The interaction is calcium dependent, and therefore the presence or absence of calcium can be used to retain and release the target cells, respectively. Another interaction that can be used in accordance with the subject invention involves the dna-K gene product of *Escherichia coli* which reversibly interacts with a recombinant protein A molecule (Nilsson et al. 1985; Hellebust et al. 1990). The interaction is dependent on adenosine triphosphate (ATP), and therefore the presence or absence of ATP can be used to release and retain the target cells, respectively.

It should be readily apparent from the above examples that the concept of the subject invention is readily applicable to any such reversible interactions between two molecules. The reversibility of the interaction allows for the separation of target cells from a plurality of cells without the need for mechanical agitation and/or enzymatic treatment to release the target cells retained at the solid support. It should also be readily apparent that the two molecules which reversibly interact can be naturally occurring or genetically engineered, chemically modified or genetically modified, etc., as long as the resulting molecules are capable of reversibly interacting with one another. For example, a calmodulin fusion protein may be used in place of "calmodulin" if the fusion protein is more easily linked to a solid support. As used herein, "calmodulin" is intended to refer to and to include such modified and fusion forms of calmodulin. The calmodulin binding peptide may be chemically altered to include a cysteine residue at the amino terminal end to more readily facilitate the attachment of the peptide to an antibody. As used herein, "calmodulin binding peptide" is intended to refer to and to include such modified calmodulin binding peptides. The invention is intended to encompass the concept of two molecules capable of reversible interaction, and as such is intended to cover slight variations in the two molecules which do not alter the reversible interaction of those two molecules. Two molecules, as used herein, are therefore intended to encompass variations made to the two molecules to facilitate attachment to a cell binding reagent and/or a solid support in accordance with the subject invention.

With an understanding of the concept of the subject invention, it should be readily apparent that any target cell for which a cell binding reagent can be identified can be separated using the subject method. A "cell binding reagent" is any molecule that is specific for a target cell. Such specificity, as used herein in this regard, means that the chosen "cell binding reagent" binds to the target cell of interest only and not to other non-target cells. The cell binding reagent may bind to a single type of cell (for example, with a protein present only on human breast cancer cells) where a single type of cell is the target cell, or the cell binding reagent may bind to a group of cells (for example, to a protein present on all human cells as opposed to mouse cells) where the group of cells are the target cells. The "cell binding reagent" may be naturally occurring or synthetically produced, or may be chemically or genetically altered from a naturally occurring form. As a further example, one could select an antibody that binds to all human immunoglobulins, or one could select an antibody that binds only to human IgM immunoglobulins. Generally, the cell binding reagent reacts with some surface feature (feature could be a cell surface protein, a cell surface polysaccharide, a cell surface receptor, etc.). The following represent examples of cell binding reagents: an antibody that specifically binds to a protein antigen specific to the target cell; a lectin that specifically binds to a polysaccharide specific to the target cell; a peptide that specifically binds to a receptor specific to the target cell; and a hormone that specifically binds to a hormone receptor specific to the target cell. This list is not intended to be limiting. Each cell binding reagent specifically binds (only binds) to a cell feature that is specific to (only present on) the target cell. This results in the specificity of the separation method, since only target cells will be attached to the cell binding reagent.

In accordance with the method of the subject invention, a target cell/cell binding reagent/first molecule/second molecule/solid support complex is formed (the first molecule reversibly binds to the second molecule as discussed above). The complex can be formed by methods known in the art and the sequence of formation is not critical to the subject invention. For example, the target cell may be reacted with the cell binding reagent, and then the resulting complex may be reacted with the first molecule. Alternatively, the cell binding reagent may first be reacted with the first molecule, and then that resulting complex may be reacted with the target cell. Similarly, the solid support may be reacted with the second molecule, and the resulting complex may be reacted with the first molecule (which may itself already be part of a target cell/cell binding reagent/first molecule complex). Alternatively, the first molecule may be reacted simultaneously with the second molecule and the solid support (again, the first molecule may itself already be part of a target cell/cell binding reagent/first molecule complex). In some instances, it may-be desirable to simultaneously react all five of the components of the target cell/cell binding reagent/first molecule/second molecule/ solid support complex. In addition, the binding of any two of the components of the complex to one another could involve the use of additional molecules. For example, an anti-cell binding reagent molecule may be used to link the first molecule to the cell binding reagent (again, the sequence of reaction is not critical).

In one embodiment, the target cell/cell binding reagent/ first molecule/second molecule/solid support complex is formed by reacting a plurality of cells with the cell binding reagent, wherein the cell binding reagent binds to target cells present within the plurality of cells forming target cell/cell binding reagent complexes; reacting the target cell/cell binding reagent complex with the first molecule to form a target cell/cell binding reagent/first molecule complex; and contacting the target cell/cell binding reagent/first molecule complex with a second molecule and the solid support, wherein the first molecule reversibly binds to the second molecule and the solid support binds to the second molecule, forming the target cell/cell binding reagent/first molecule/ second molecule/solid support complex. As indicated above, and in a presently preferred embodiment, the reaction of the target cell/cell binding reagent complex with the first molecule to form a target cell/cell binding reagent/first molecule complex can comprise linking an anti-cell binding reagent molecule to the first molecule and reacting the linked anti-cell binding reagent molecule with the cell binding reagent, so that the target cell/cell binding reagent/first molecule complex further includes an anti-cell binding reagent molecule linking the cell binding reagent to the first molecule. The anti-cell binding reagent molecule can be, for example, an antibody, which can be covalently-linked to the first molecule.

Since genetic engineering techniques have progressed, it should be readily apparent that the cell binding reagent could be constructed to contain the first molecule. For example, if the cell binding reagent is an antibody and the molecule that reversibly interacts is a peptide, an antibody can be produced which includes the peptide sequence as part of the antibody. In another example, a bacteriophage could be the cell binding reagent and the peptide sequence could be displayed by the phage. Any protein ligand (which will bind to target cells which have a receptor for the ligand) could also be engineered to include the peptide sequence.

As used herein, "reacting" refers to allowing the two or more elements (for example, the plurality of cells and the cell binding reagent) to come into contact with one another under conditions such that the two or more elements bind to one another (for example, the cell binding reagent binds to target cells present within the plurality of cells). This reaction can take place in a test tube, a well, on a plate, in a flask, etc. Standard laboratory procedures are used to perform this reaction.

The solid support can have attached thereto the second molecule, and the first molecule reversibly binds to the second molecule when the first and second molecules come into contact with one another. Target cells are thereby reversibly attached to the solid support. As above, the second molecule can be attached to the solid support using any methods known in the art. In one embodiment exemplified herein, the solid support is a streptavidin solid support and the second molecule is attached to the streptavidin solid support with biotin. As indicated above, if the second molecule is calmodulin, it may be desirable to form a calmodulin fusion protein that is readily crosslinked to a solid support. The particular method of attachment of the second molecule to the solid support is best determined based on the solid support and second molecule chosen. Solid supports come in various forms as is known in the art. Solid supports include tubes, beads, wells, plates, etc. The solid support may be magnetic or non-magnetic. These various forms of solid support are known in the art and a suitable form of solid support can be readily chosen for use in accordance with the subject invention.

Having allowed the target cells to bind to the solid support, non-target cells not attached to the solid support are then removed. This can be accomplished by washing with a buffer. For example, if the solid support is beads in a column, a buffer can be passed through the column to remove non-bound non-target cells. The cells of the plurality of cells which are not target cells (for example, the cells of the plurality of cells that are not bound to the first molecule via the cell binding reagent) are thus removed (for example, removed from the column).

This leaves the target cells attached to the solid support via the first molecule/second molecule reversible interaction.

The binding of the first molecule to the second molecule is then reversed, thereby releasing the target cells as separate cells from the plurality of cells. For example, if the binding of the first molecule to the second molecule requires the presence of another molecule, the complex is formed in the presence of that molecule and the reversal of binding occurs by removing that molecule. This aspect of the subject invention is readily illustrated by the use of calmodulin and a calmodulin binding peptide as the first and second molecules. The calmodulin reversibly binds to the calmodulin binding peptide in the presence of calcium. Therefore, the complex is formed in the presence of calcium. The binding of the first molecule to the second molecule is reversed by removing calcium, thereby releasing the target cells. The calcium can be removed by using a calcium chelator (the third molecule), such as EGTA. Alternatively, the reversal of binding may occur by adding another molecule. As an illustration of this aspect of the subject invention, the binding of the dna-K gene product of *Escherichia coli* to recombinant protein A (Nilsson et al. 1985; Hellebust et al. 1990) is reversed by the addition of ATP.

Having thus described the method of the subject invention, its use should be readily apparent. The method can be used in research and/or clinical settings wherever the separation of a target cell from a plurality of cells is desirable. If a cell binding reagent can be identified then the target cell can be separated from a plurality of cells. For example, the plurality of cells may be bone marrow cells for transplantation and the target cells would be T cells, tumor cells, or stem progenitor cells. These are all cells that one may desire to isolate from bone marrow cells generally. T cells and tumor cells may be removed from bone marrow so that the marrow can be reimplanted (transplanted) back into an individual (or into another individual). Stem progenitor cells are often desirable cells to reimplant (or transplant) and thus are also a target cell of interest in transplantation technology.

The following examples relate to one embodiment of the method of the subject invention. This embodiment is based on the calcium-dependent interaction of calmodulin (CM) with a calmodulin-binding peptide (CBP). This system utilizes an indirect method to label the target cell population. Cells are first labeled with a primary monoclonal antibody directed to a specific cell surface antigen, then with a secondary affinity reagent, consisting of a polyclonal goat anti-mouse IgG (GAM-IgG) that has been cross-linked to a CBP derived from the sequence of the rabbit skeletal muscle myosin light chain kinase. In the presence of $Ca^{2+}$, the CBP on the cells labeled with GAM-IgG-CBP binds to biotinylated calmodulin (CM-Biotin) with high affinity. The target cells are then captured with a solid-phase streptavidin. The unbound non-target cells are washed away and the immobilized target cells are released by chelating $Ca^{2+}$ with EGTA. The specificity of the GAM-IgG-CBP and CM-Biotin and the feasibility of using this system to separate cells was demonstrated using the KG-1 human acute myelogenous leukemia cell line. KG-1 cells were fractionated on the basis of cell surface expression of HLA-DR. The cell selection reagents and the cell separation process did not affect KG-1 cell viability while cells selected by this procedure were 90% pure with a yield of 75%. This cell separation system also was used for rare cell isolation from normal human peripheral blood mononuclear cells. T cells expressing the Vβ5 T cell receptor, which represent <5% of the unfractionated cells, were isolated with 89% viability, 72% purity, 80% yield and retained the ability to respond to activation signals as measured by blast transformation. The results from this study show that a cell selection system based on the reversible interaction between CM and a CBP can be applied to gently and efficiently isolate cells from a heterogeneous starting population that are free of the solid matrix and have not been exposed to the stresses of mechanical or enzymatic release.

The CM/CBP cell separation system exemplified herein utilizes an indirect method to fractionate cells, making it highly versatile as well as compatible with existing cell separation technologies. Because this CM/CBP cell separation system utilizes an indirect labeling method, it is more labor-intensive than directly labeling the cells for isolation. Nevertheless, cells can be isolated by this method in less than 4hr. Efforts to simplify the cell separation process and subsequent analysis of isolated cells can use a pre-assembled labeling complex consisting of anti-Vβ5-FITC:GAM-IgG-CBP:CM-Biotin:MACS SA microbeads. Other approaches to simplify cell separation and analysis involve preparation of CBP-conjugated, fluorochrome-labeled primary antibodies to make labeling of cells less time consuming and allow assessment of target cell purity without additional washing and staining steps. Moreover, the CBP can be conjugated to ligands other than monoclonal antibodies, such a lectins, cytokines, peptides or drugs, that differentially recognize a cell surface determinant and define a specific subpopulation of cells. A CM-binding domain can also be incorporated into the coding regions for affinity reagents generated by phage display (Griffiths, 1993) or transgenic immunoglobulin (Lonberg and Huszar, 1995) technologies. Expression of the CBP domain in recombinant phage or transgenic immunoglobulins is useful for both purification and their adaptation to cell separation. Additional improvements in the CM/CBP cell separation system include direct coupling of CM to a solid matrix with CM retaining the ability to bind and release CBP-labeled cells.

Materials and Methods

Reagents Goat anti-mouse IgG (GAM-IgG) was from Zymed Laboratories (So. San Francisco, Calif.) and unlabeled anti-HLA-DR (clone TÜ36, $IgG_{2b}$), anti-human Vβ5 T cell receptor (TCR) (clone MH3-2, $IgG_{2a}$), anti-human CD3-cychrome (clone HIT3a, $IgG_{2a}$) and isotype controls were obtained from Pharmingen (San Diego, Calif.). Fluoresceinated (FITC) anti-HLA-DR (clone H279, $IgG_{2a}$) was obtained from Coulter (Hialeah, Fla.). Anti-human CD3 (clone OKT3, $IgG_{2a}$) used for T cell activation was from American Type Culture Collection (ATCC) (Rockville, Md.); Dulbecco's phosphate buffered saline (PBS) was from Biowhittiker (Walkersville, Md.); bovine brain CM, CM-FITC, human gamma globulins, Cohn fraction II (HuIgG), $CaCl_2$, propidium iodide and 2-(4-hydroxyazobenzene) benzoic acid (HABA) were from Sigma Chemical Co. (St. Louis, Mo.). $NaN_3$ was from Fisher Co. (Springfield, N.J.); Sephadex G-25 was from Pharmacia Co. (Piscataway, N.J.) and sulfosuccinimidyl-4-(N-maleimidomethyl)cyclohexane-1-carboxylate (S-SMCC), sulfosuccinimidyl-6-(biotinamido) hexanoate (S-NHS-LC-Biotin) and Coomassie Plus Protein Assay Reagent were from Pierce (Rockford, Ill.). The CBP was synthesized by the Wadsworth Center peptide synthesis core facility and was based on the sequence of the rabbit skeletal muscle myosin light chain kinase CM-binding domain (Takio et al. 1986) to which an amino-terminal cysteine residue was added. M-280 Streptavidin (SA) Dynabeads were obtained from Dynal (Oslo, Norway); MACS SA microbeads were from Miltenyi Biotec (Auburn, Calif.); SA-FITC was obtained from TAGO (Burlingame, Calif.); EGTA was from Fluka Chem. Co. (Ronkonkoma, N.J.); Ficoll-Hypaque was from Pharmacia (Uppsala, Sweden) and Immulan goat anti-human IgG polystyrene beads were from Biotecx Laboratories (Houston, Tex.).

Cells The human acute myelogenous leukemia cell line KG-1 (Koeffler and Golde, 1978) was obtained from ATCC (Rockville, Md.). KG-1 cells were passed weekly in Iscove's modified Dulbecco's medium containing 4 mM L-glutamine, 20 μg/ml gentamicin-$SO_4$ (complete IMDM) and 20% fetal bovine serum (FBS) (Hyclone, Logan, Utah.) and incubated at 37° C. in 7% $CO_2$. KG-1 cells in log-phase growth were used in all experiments. Human peripheral blood was obtained from healthy volunteers following informed consent according to an Institutional Review Board-approved protocol. Peripheral blood mononuclear cells (PBMC) were prepared by density gradient centrifugation over Ficoll-Hypaque cushions. Fractions of PBMC enriched or depleted of T cells were prepared using Immulan columns of goat anti-human IgG polystyrene beads using the procedure provided by the manufacturer (T cell-enriched fraction 82% $CD3^+$, ≦2% $CD14^+$or $CD19^+$). For use as accessory cells in T cell activation, the T cell-depleted PBMC fraction was recovered and γ-irradiated with 3000 cGy at 4° C. PC using a $^{137}Cs$ source (Isomedix, Parsippany, N.J.) at a dose rate of 300 cGy/min and a cell density of $5\times10^6$ cells/ml. Following irradiation, the cells were diluted to $3\times10^5$/ml in RPMI 1640 containing 1× MEM nonessential amino acids, 1× pyruvate, 0.9% $NaHCO_3$, 2.4 mM L-gln, 10 μg/ml gentamicin-$SO_4$ and 10% FBS (complete RPMI 1640/ 10% FBS). In some experiments, $2\times10^4$ irradiated accessory cells, in 0.5 ml complete RPMI 1640/10% FBS were added to wells of 24 well plates previously coated with 100 μg/ml anti-CD3 (OKT3) in PBS for 2 hr at 22° C. and washed 3× with PBS. Cells were incubated overnight at 37° C. in 7% $CO_2$ before use. Aliquots of PBMC, from each fractionation step, were added to OKT3-coated wells±irradiated accessory cells and cultured for 4 days at 37° C., 7% $CO_2$ and then one additional day in uncoated wells to allow TCR expression to recover as described (Kappler et al. 1989).

Chemical Syntheses To maximize versatility of CM/CBP-based cell selection reagents, the CBP was cross-linked to a secondary anti-immunoglobulin reagent using the heterobifunctional crosslinker S-SMCC. Briefly, 90 μg of freshly prepared S-SMCC (18 μl of a 5 mg/ml stock in PBS) was added to 830 μl 0.75 mg/ml GAM-IgG (50:1 molar ratio) PBS, pH 7.4 and rocked for 1 hr at 22° C. Uncoupled S-SMCC was removed by passage over a 0.5×25 cm G-25 column equilibrated with PBS, pH 6.8 at room temperature and the GAM-IgG-S-SMCC conjugate-containing fractions were detected using the Coomassie Plus Protein Assay Reagent and pooled. Then 33 μl of 25 mg/ml CBP in PBS, pH 6.8, was added to the pooled GAM-IgG-S-SMCC fractions at a molar ratio of 65 CBP to 1 GAM-IgG-S-SMCC and rotated overnight at 4° C. Excess CBP was removed by dialysis against PBS/0.02% $NaN_3$. CM was modified by biotinylation (CM-Biotin) to make it compatible with existing SA-based target cell separation media. CM-Biotin was synthesized by adding 29 μl of 5 mg/ml freshly prepared S-NHS-LC-Biotin to 860 μg CM in 400 μl ice cold 50 mM HEPES/1mM $CaCl_2$/0.25M NaCl, pH 7.5 and rotating for 2 hr at 4° C. Uncoupled S-NHS-LC-Biotin was removed by passage of the reaction mixture over a 0.5×25 cm G-25 column equilibrated with D-PBS/1 mM $CaCl_2$/0.02% $NaN_3$ at 4° C. CM-Biotin-containing fractions were pooled and the CM to biotin molar ratio was calculated to be 1.6 by the spectrophotometric determination of the protein concentration and the displacement of HABA from avidin as described (Green, 1965). CM-Biotin:SA-FITC was made by combining CM-Biotin and SA-FITC at a molar ratio of 4 CM-Biotin to 1 SA-FITC and incubating on ice for more than 1 hr before use.

Flow Cytometry: Unless otherwise indicated all labeling procedures were conducted at 4° C. and incubations were for 30 min in PBS/0.5% heat inactivated HuIgG/0.02% $NaN_3$/1 mM $CaC_2$ ($Ca^{2+}$-buffer) and the cells were washed twice with the same buffer or with PBS/0.02% $NaN_3$/1 mM EGTA (EGTA-buffer) and pelleted by centrifugation for 7.5min at 400×g. Staining of the cells was performed with 1 μg of each antibody, 0.2 μg of CM or CM-FITC and/or 1 μg of CM-Biotin:SA-FITC per $10^6$ cells. To demonstrate reversibility of CM-Biotin:SA-FITC binding, some samples were split and washed in either $Ca^{2+}$- or EGTA-buffer. To restain fractions of selected cells, cells were washed twice with EGTA-buffer, once with $Ca^{2+}$-buffer and restained with CM-FITC or CM-biotin:SA-FITC. Alternatively, PBMC were cultured for four days with solid-phase anti-CD3 and irradiated accessory cells, transferred to uncoated wells for an additional 18hr and then stained with anti-Vβ5-FITC and anti-CD3 cychrome. Samples were stained with propidium iodide to assess viability and analyzed using a FACSCAN flow cytometer (Becton Dickinson, San Jose, Calif.).

Cell Selection: KG-1 cells were labeled with anti-HLA-DR while PBMC were labeled with anti-Vβ5 followed by GAM-IgG-CBP and CM-Biotin as described in the flow cytometry section above. Target cells were either captured with SA-coated magnetic Dynabeads (20 beads/cell, previously washed 3× with PBS/1 mM $CaCl_2$/0.02% $NaN_3$ and resuspended in 75 μl $Ca^{2+}$-buffer) or MACS SA microbeads (10 μl suspension/$10^7$ cells in 90 μl) with very similar results. Cell selection with Dynabeads was performed as follows: After the final wash, the labeled cells were resuspended in 125 μl $Ca^{2+}$-buffer and $8.2\times10^6$ cells were gently mixed with the washed SA Dynabeads. The bead/cell suspension was rotated axially at approximately 25 rpm for 1 hr at 4° C. The target cells captured by the beads were separated from the unbound cells using a magnet. Unattached cells trapped in the magnetic beads were removed by washing twice with 200 μl $Ca^{2+}$-buffer and combined with the target-depleted fraction. The cells bound to the beads were released by gentle agitation with four 200 μl aliquots of EGTA-buffer. Prior to labeling with the MACS SA microbeads, cells were passed over a miniMACS column to remove adherent cells and cell aggregates. Cells were labeled with MACS SA microbeads, washed, passed over a second miniMACS column twice and washed with 3×500 μl $Ca^{2+}$-buffer. Column-bound target cells were released and collected in a separate tube containing 0.5 ml PBS/0.5% human IgG/0.02% $NaN_3$ as follows. The column was rinsed with 3×250 μl EGTA-buffer, incubated with the EGTA-buffer for 5 min at room temperature, then 1ml of EGTA-buffer was pushed through with a miniMACS column piston at approximately 12 ml/min. Aliquots of pre-selection and target-depleted or -enriched cells were restained for flow cytometry as described above to assess the purity of the separated cells. In addition, the cell numbers in the cell fractions were determined using a Coulter ZM cell counter to assess cell recovery and yield.

EXAMPLE I

Figure 2:
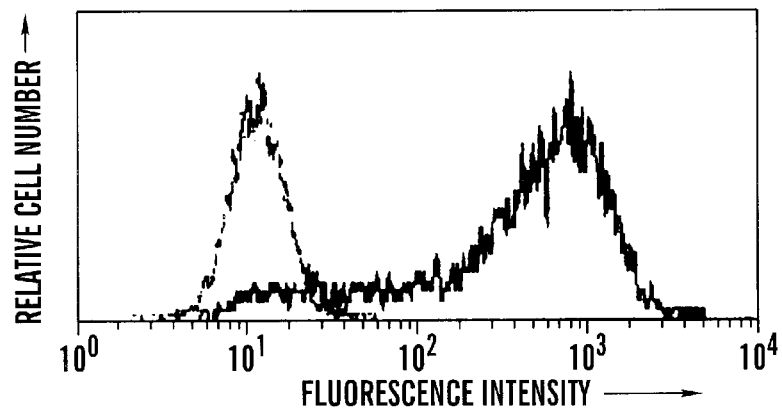
FIGS. 2–5 illustrate the specificity and reversibility of CM/CBP cell selection reagents. KG-1 cells were stained and analyzed as described in the Materials and Methods section. Specific HLA-DR staining is shown with anti-HLA-DR-FITC (FIG. 2), anti-HLA-DR, GAM-IgG-CBP and CM-Biotin:SA-FITC (FIG. 4) or anti-HLA-DR, GAM-IgG-CBP and CM-FITC (FIG. 5). Reagent specificity controls were mouse $IgG_{2a}$-FITC (FIG. 2), anti-HLA-DR, GAM-IgG-CBP, unbiotinylated CM and SA-FITC (FIG. 3, dimmer histogram), GAM-IgG-CBP and CM-Biotin:SA-FITC without anti-HLA-DR (FIG. 3, brighter histogram) and anti-HLA-DR, unconjugated GAM-IgG and CM-Biotin:SA-FITC (FIG. 4). The dimmer histogram in FIG. 5 was the result of washing cells stained with anti-HLA-DR, GAM-IgG-CBP and CM-Biotin:SA-FITC with EGTA-buffer.
Figure 3:
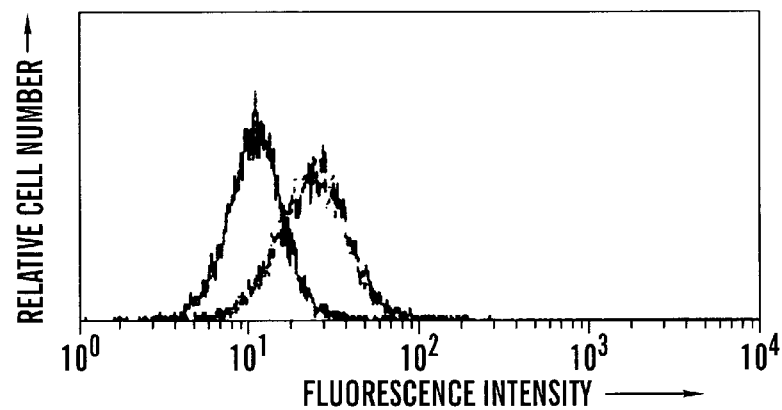
Figure 4:
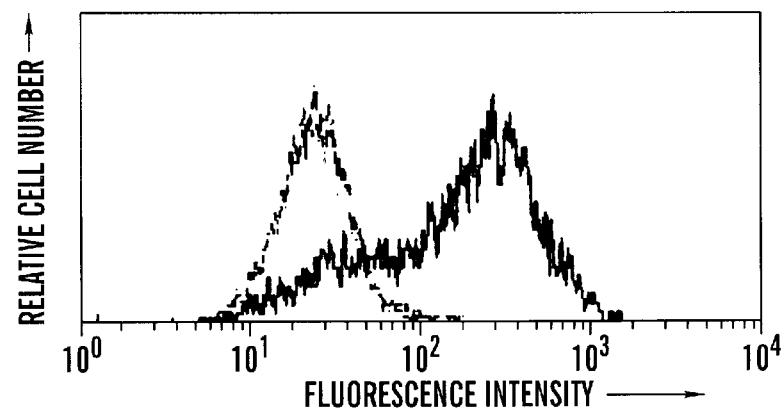
Figure 5:
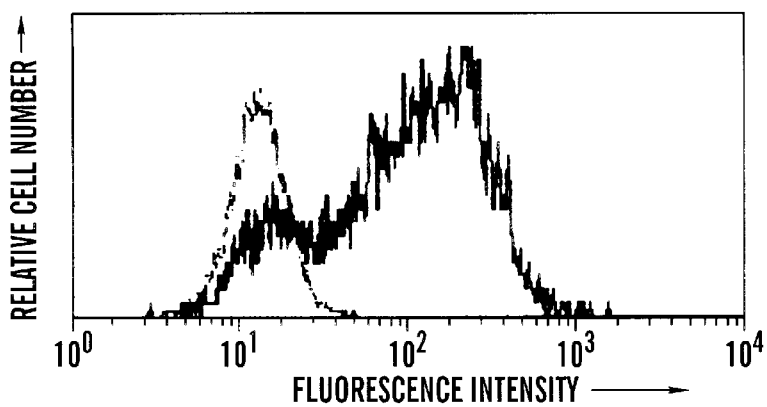

Specificity and reversibility of CM-Biotin and GAM-IgG-CBP cell selection reagents. KG-1 cells were used to test the specificity of the cell selection reagents. The KG-1 AML cell line, in log-phase growth, is heterogeneous with respect to cell surface expression of the major histocompatibility complex HLA-DR molecule. Direct staining of KG-1 cells with anti-HLA-DR-FITC showed that 80% of the cells were HLA-$DR^{30}$ relative to the FITC-conjugated isotype control antibody (FIG. 2). Similar percentages of HLA-$DR^{30}$ cells were detected by indirect staining in $Ca^{2+}$-buffer with unconjugated anti-HLA-DR followed by GAM-IgG-CBP and either CM-Biotin:SA-FITC or CM-FITC (FIGS. 4 and 5, 77% and 78%, respectively). The differences between the mean fluorescence intensities (MFIS) correlate with the differences in FITC/protein (F/P) ratios of HLA-DR-FITC, SA-FITC and CM-FITC (F/P=10, 5.5 and 0.8, respectively). The specificity of the GAM-IgG-CBP and CM-Biotin:SA-FITC reagents is shown in FIGS. 2–5. In the absence of anti-HLA-DR, the MFI of GAM-IgG-CBP/CM-Biotin:SA-FITC stained cells were reduced by an order of magnitude (FIG. 4). Similar reductions in MFIs were observed if GAM-IgG-CBP was replaced with GAM-IgG (FIG. 3, brighter histogram) or CM-Biotin was replaced with CM (FIG. 3, dimmer peak). Human PBMC also exhibited low background binding of CM-Biotin or GAM-IgG-CBP. The reversibility of CM binding to GAM-IgG-CBP when $Ca^{2+}$ was chelated was demonstrated using a sample of KG-1 cells stained with anti-HLA-DR, GAM-IgG-CBP and CM-FITC where half of the cells were washed in $Ca^{2+}$-buffer and the other half in EGTA-buffer. As shown in FIG. 5, the specific HLA-DR staining observed in the presence of $Ca^{2+}$ was reduced to background levels following the EGTA wash. Washing with EGTA-buffer did not reduce cell viability and had a comparable reversing effect on CM-Biotin:SA-FITC staining.

EXAMPLE II

Figure 6:
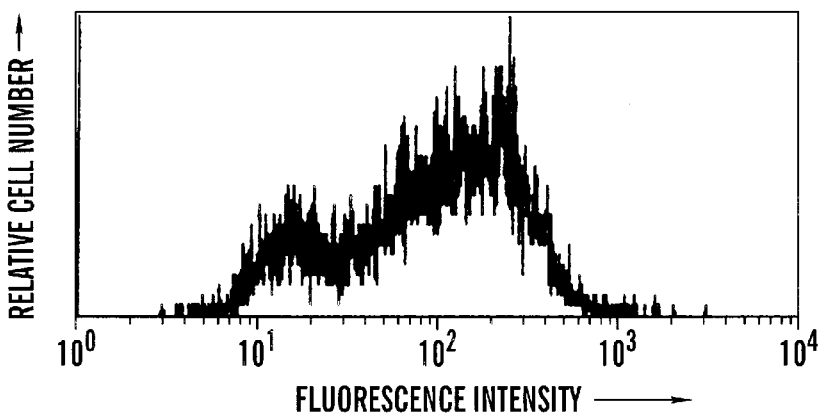
FIGS. 6 and 7 illustrate flow cytometric analysis of KG-1 cells fractionated using the CM/CBP cell separation system on the basis of HLA-DR expression. KG-1 cells were labeled with anti-HLA-DR, GAM-IgG-CBP, CM-Biotin, MACS SA microbeads and magnetically separated. Aliquots of cells, removed prior to selection or from the HLA-DRdepleted or -enriched fractions, were washed with EGTA-buffer, re-equilibrated with Ca²⁺, restained with CM-FITC and analyzed by flow cytometry. HLA-DR staining of cells before selection is shown in FIG. 6 and that in the HLA-DR-depleted and -enriched fraction is shown in the overlaid histograms in FIG. 7.
Figure 7:
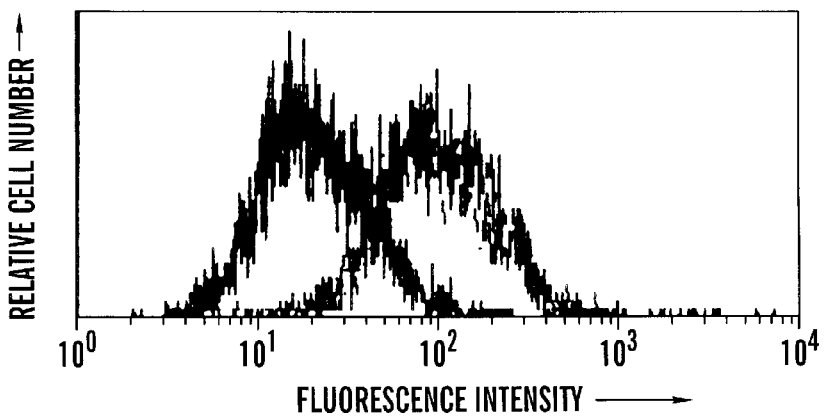
Figure 8:
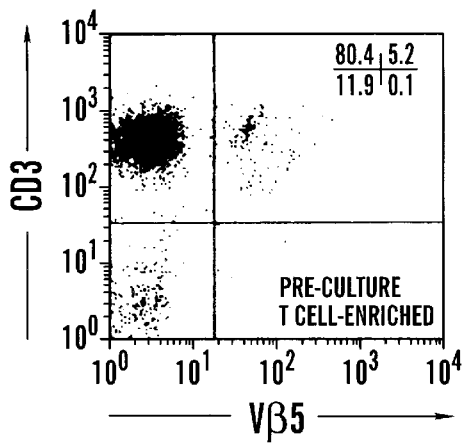
FIGS. 8–12 illustrate flow cytometric analysis of human T cell fractions before and after labeling with the CM/CBP cell separation reagents or Vβ5-targeted fractionation. Unlabeled cells of the T cell-enriched fraction were analyzed for Vβ5 and CD3 expression prior to (FIG. 8) or following (FIG. 9) 4 days of culture with solid phase anti-CD3 and irradiated accessory cells. Cells, labeled with the CM/CBP selection reagents before fractionation (FIG. 10) or from the Vβ5-depleted (FIG. 11) or -enriched (FIG. 12) fractions were all analyzed post-culture with anti-CD3 and irradiated accessory cells.

Selection of HLA-DR$^{30}$ $^{KG}$-1 cells. The feasibility of using the CM/CBP cell separation system to fractionate KG-1 cells into HLA-DR-depleted and -enriched subpopulations was tested. KG-1 cells were labeled with anti-HLA-DR followed by GAM-IgG-CBP, CM-Biotin and SA-magnetic beads. The target cells were immobilized on a magnet and nontarget cells were removed by washing in the presence of $Ca^{2+}$. Without removing the immobilized cells from the magnetic field, the target cells were released by chelating $Ca^{2+}$ with EGTA-buffer. Analysis of restained cells by flow cytometry showed that the CM/CBP selection reagents and EGTA were not cytotoxic and the HLA-DR-enriched fractions averaged a purity of 90% HLA-DR$^{30}$ while the HLA-DR-depleted fraction was reduced to 13% HLA-DR$^{30}$ (Table I). Using the absolute numbers of HLA-DR$^{30}$ cells in the HLA-DR-enriched and Pre-selection fractions, a 75% yield was calculated. To ensure that the target cells were actually dissociated from the magnetic beads, an aliquot of target cells was re-applied to the magnet. Less than 10% of the released cells were capable of binding to the magnet following EGTA treatment. Reversibility of the CM/CBP interaction was also demonstrated. HLA-DR$^{30}$ cells in the Pre-selection (FIG. 6) and HLA-DR-enriched and -depleted (overlaid histograms, FIG. 7) fractions could be restained with CM-Biotin: SA-FITC following EGTA wash and re-equilibration with $Ca^{2+}$. These results showed that the reversible CM/CBP interaction could be used to gently and efficiently separate cells.

EXAMPLE III

Figure 9:
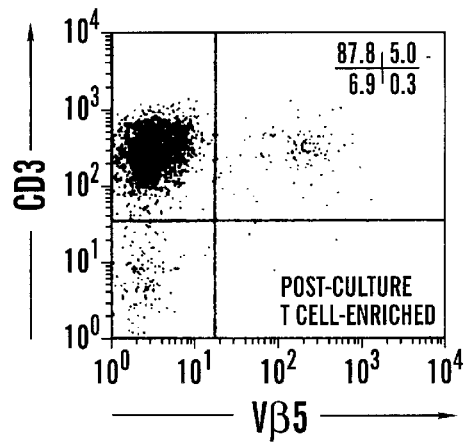
Figure 10:
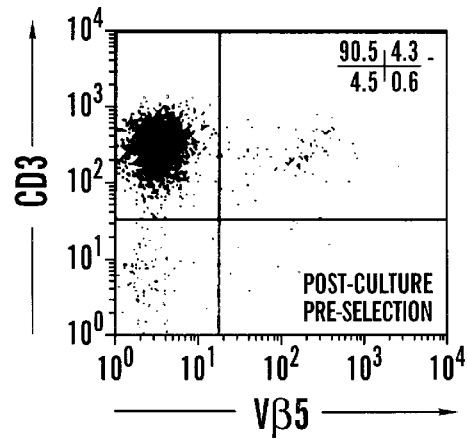
Figure 11:
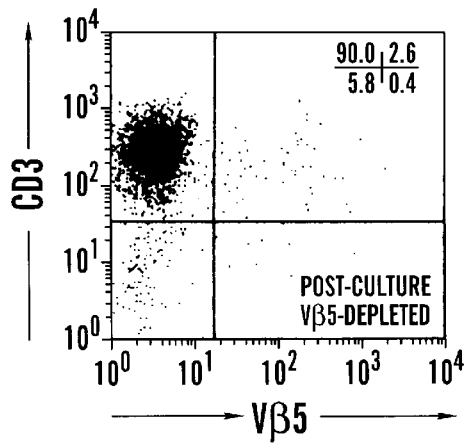
Figure 12:
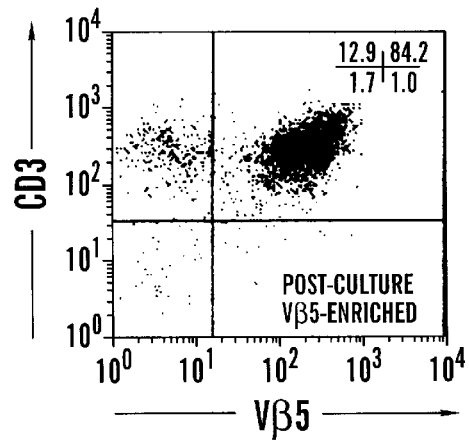
Figure 13:
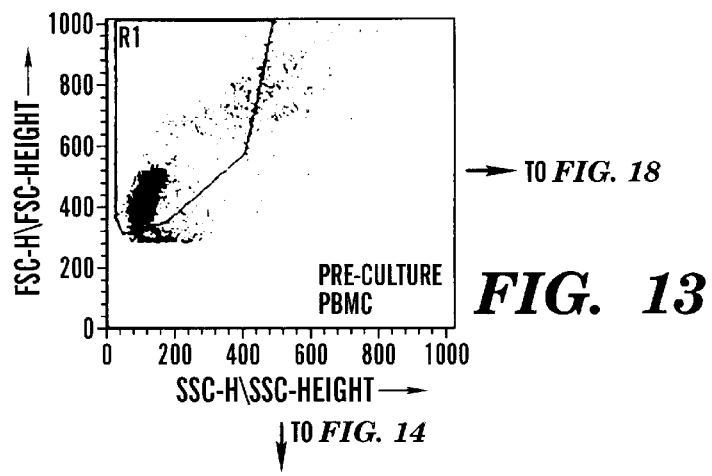
FIGS. 13–22 illustrate the effects of labeling with the CM/CBP cell separation reagents and subsequent fractionation on blast transformation following 4 days of culture with solid-phase anti-CD3 and irradiated accessory cells. Light scatter properties of PBMC (FIG. 13 and FIG. 18), cells from the T cell-enriched fraction, prior to (FIG. 14 and FIG. 19) or following labeling with the cell separation reagents (FIG. 15 and FIG. 20) and depleted (FIG. 16 and FIG. 21) or enriched (FIG. 17 and FIG. 22) for Vβ5-expressing cells were determined before (FIGS. 13–17) or after (FIGS. 18–22) 4 days of culture with solid-phase anti-CD3 and irradiated accessory cells.
Figure 14:
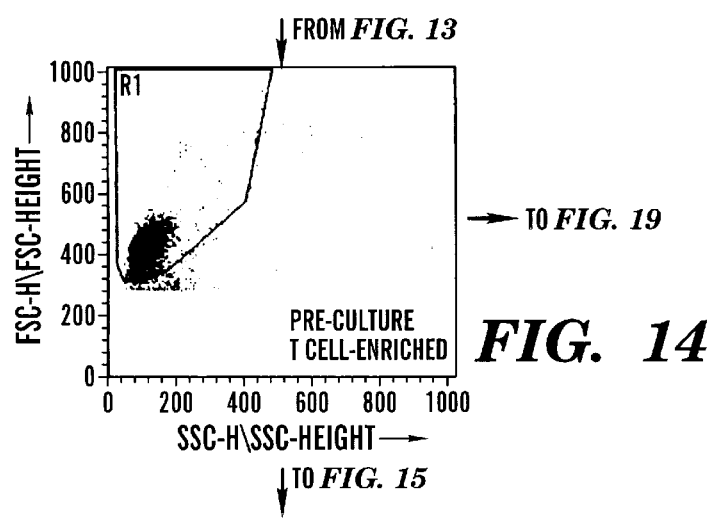
Figure 15:
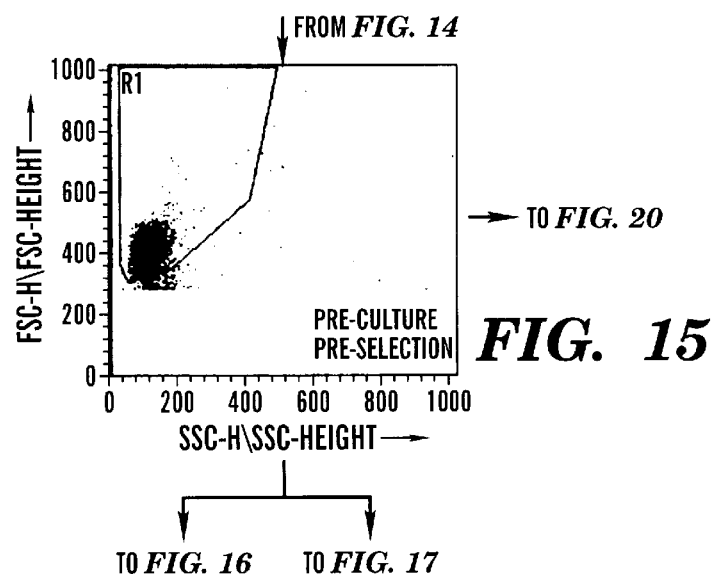
Figure 17:
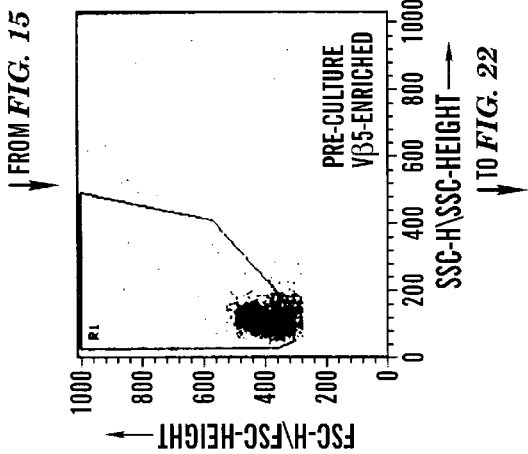
Figure 22:
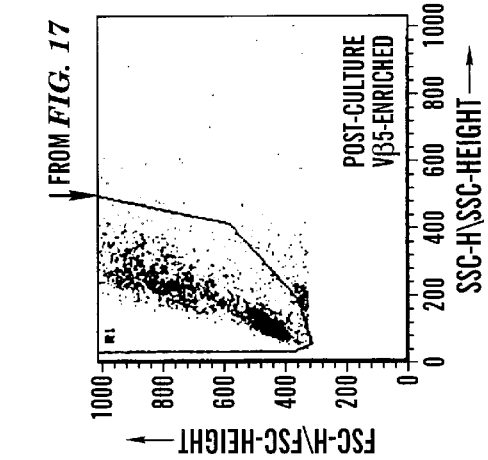
Figure 16:
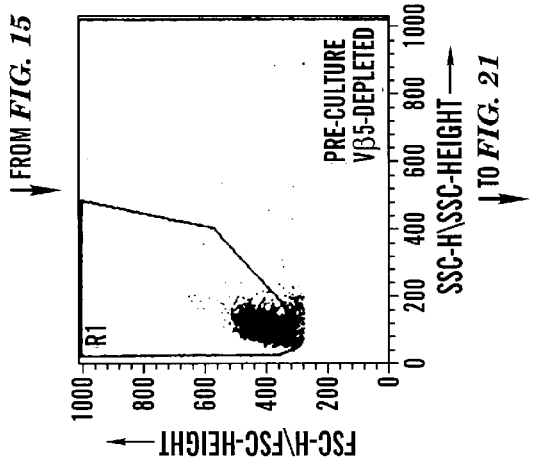
Figure 21:
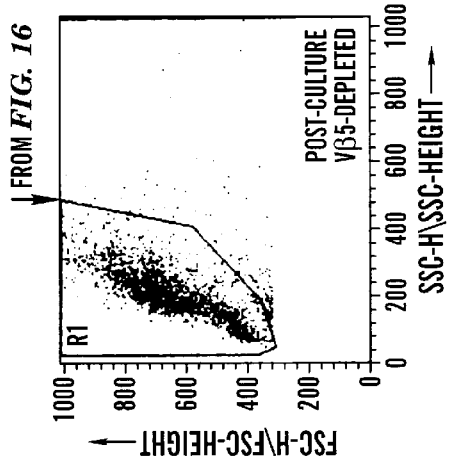
Figure 18:
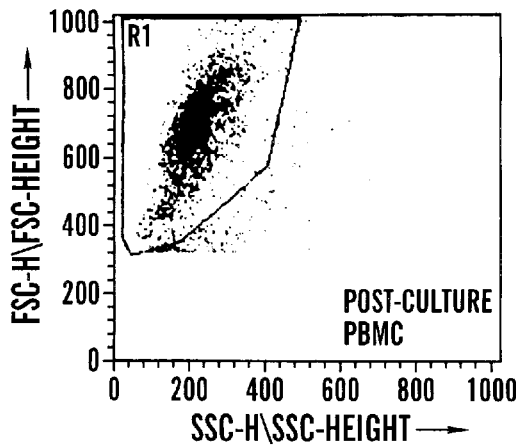
Figure 19:
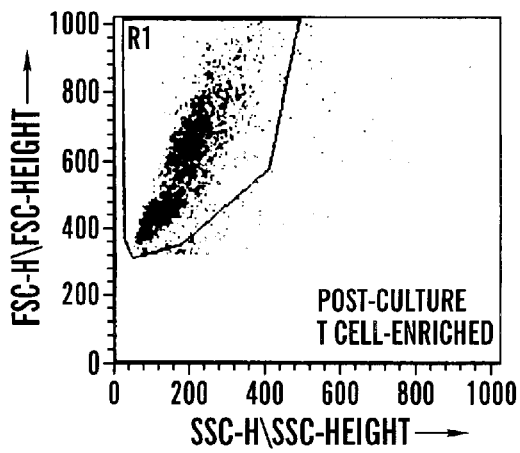
Figure 20:
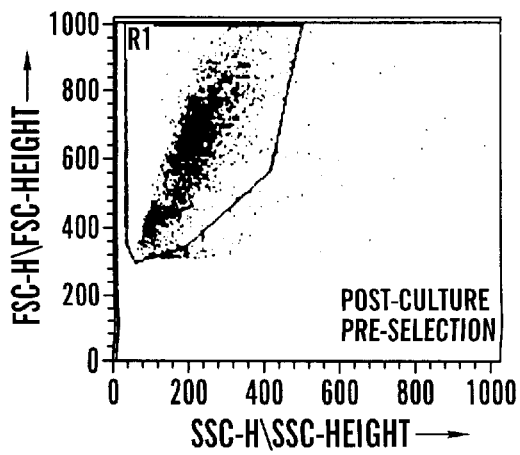

Rare cell separation using the CM/CBP cell selection system. The capabilities of the CM/CBP cell selection system were more rigorously tested by targeting a relatively low frequency subpopulation of cells from normal human PBMC for isolation. T cells expressing TCR β subunits derived from the Vβ5S2 or Vβ5S3 gene segments that represent two of the approximately 52 possible Vβ gene segments (Akolkar et al. 1997) were chosen as a test subpopulation for purification. These cells, which represent approximately 3–5% of the lymphocytes in PBMC (Kappler et al. 1989) are recognized by the Vβ5S2/S3-specific monoclonal antibody, MH3-2 (Posnett et al. 1996; Peyrat et al. 1996). Nonspecifically adherent cells were removed by first enriching for T cells and then passing the T cell-enriched fraction, labeled with anti-Vβ5; GAM-IgG-CBP and CM-Biotin, over a magnetic column in $Ca^{2+}$-buffer. The cells were then labeled with MACS SA microbeads and loaded onto a second magnetic column and washed with $Ca^{2+}$-buffer. Selected cells bound to the column were eluted in EGTA-buffer. It has been previously reported that the relative proportion of Vβ5$^+$ T cells present in freshly isolated PBMC were unaffected by culturing (Kappler et al. 1989); the results shown in FIGS. 8–12 and Table II confirmed this observation. In addition, labeling cells with the cell separation reagents prior to 4 days of culture with solid-phase anti-CD3±irradiated accessory cells did not significantly influence the percentages of CD3$^+$ or Vβ5$^+$ cells (FIGS. 9 and 10 and Table II). FIGS. 8–12 also illustrate the ability of this CM/CBP-based cell separation system to yield a PBMC subpopulation highly enriched for Vβ5$^+$ target cells. The performance of the CM/CBP-based cell selection system is summarized in Table III. Vβ5 selection had no significant effect on cell viability determined immediately following fractionation and, on average, Vβ5$^+$ cells were enriched by 20-fold to a purity of 72% with an 80% yield. Furthermore, compared with unlabeled T cells (FIGS. 14 and 19), in the presence of both irradiated accessory cells and solid-phase anti-CD3, unfractionated cells labeled with the CM/CBP cell selection reagents (FIGS. 15 and 20) or Vβ5-depleted or -enriched cells (FIGS. 16 and 21 and 17 and 22), exhibited similar abilities to undergo blast transformation typical of T cell activation. Taken together, these results show that the CM/CBP cell selection system can generate a functional high purity target cell population without significant cytotoxicity.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE I

Selection of HLA-DR$^+$ KG-1 cells using calmodulin/calmodulin-binding peptide affinity reagents.[a]

| Cell Fraction | Viability | Percentage HLA-DR$^+$ | Yield[b] |
|---|---|---|---|
| Pre-selection | 94 (1) | 76 (1) | N.A.[c] |
| HLA-DR-depleted | 95 (2) | 13 (8) | N.A. |
| HLA-DR-enriched | 96 (5) | 90 (3) | 75 (2) |

[a]Cells were labeled, selected, re-labeled and analysed as described in the text. The data shown represent the means and standard deviations (in parentheses) from the results of two independent experiments.

$$^b\text{Yield} = \frac{\text{number of anti-HLA-DR:GAM-IgG-CBP:CM-FITC positive cells in the HLA-DR-enriched fraction}}{\text{number of anti-HLA-DR:GAM-IgG-CBP:CM-FITC positive cells in Pre-selection fraction}} \times 100$$

[c]N.A. — not applicable

TABLE II

Effects of labeling with selection reagents and culturing on CD3[+] and Vβ5[+] cell frequencies.[a]

|  | Pre-culture, unlabeled CD3[+] | Vβ5[+] | Post-culture, unlabeled CD3[+] | Vβ5[+] | Post-culture, labeled CD3[+] | Vβ5[+] |
|---|---|---|---|---|---|---|
| Expt. 1 | 78 | 4.5 | 79 | 4.2 | 82 | 3.3 |
| Expt. 2 | 83 | 2.6 | 93 | 4.2 | 94 | 4.0 |
| Expt. 3 | 86 | 5.2 | 93 | 5.0 | 95 | 4.3 |
| x(s)[b] | 82(4.0) | 4.1 (1.3) | 88(8.1) | 4.5 (0.5) | 90(7.2) | 3.9(0.5) |

[a]Where indicated, cells were labeled with selection reagents, cultured, stained with anti-Vβ5-FITC and anti-CD3-cychrome and analyzed as described in the text.
[b]Paired t-test analyses of CD3[+] and Vβ5[+] cell frequencies between the pre- and post-culture or the unlabeled and labeled groups demonstrated no statistically significant differences ($P > 0.06$).

TABLE III

Selection of Vβ5[+] T cells using calmodulin/calmodulin-binding peptide affinity reagents.[a]

| Cell Fraction | Viability | Percentage Vβ5[+] | Yield[b] | Enrichment Factor |
|---|---|---|---|---|
| Pre-selection | 95 (2) | 4.5 (0.5) | N.A.[c] | N.A. |
| Vβ5-depleted | 93 (4) | 2.3 (0.9) | N.A. | N.A. |
| Vβ5-enriched | 89 (10) | 72 (11.5) | 80 (7) | 20 (3) |

[a]Cells were labeled, selected, cultured, re-labeled and analysed as described in the text. The data shown represent the means and standard deviations (in parentheses) from the results of three independent experiments.

$$^b\text{Yield} = \frac{\text{number of } V\beta 5^+ \text{ cells in the } V\beta 5\text{-enriched fraction}}{\text{number of } V\beta 5^+ \text{ cells in the Pre-selection fraction}} \times 100$$

[c]N.A. — not applicable

REFERENCES

Akolkar, P. N., et al., In:M. S. Leffel, A. D. Donnenberg and N. R. Rose (Eds.), Handbook of Human Immunology, CRC Press, Boca Raton, p. 567 (1997).
Bensinger, W. I., et al., J Clin Apheresis 5:74 (1990).
Berenson, R. J., et al., Cancer Investigations 14:589 (1996).
Egeland, T., et al., Transplantation Proceedings 25:1261 (1993).
Gee, A. P., Immunomethods 5:232 (1994).
Green, N. M., Biochemical Journal 94:23c (1965).
Griffiths, A. D., Current Opinion in Immunology 5:263 (1993).
Hellebust, H., et al., J Bacteriol 172:5030–5034 (1990).
Hopp, T. P., et al., Bio/Technology 6:1204–1210 (1988).
Kappler, J., et al., Science 244:811 (1989).
Klee, C. B. and Vanaman, T. C., Advances in Protein Chemistry 35:213 (1982).
Knappik, A., and Pluckthun, A., BioTechniques 17:754–761 (1994).
Koeffler, H. P. and Golde, D. W., Science 200:1153 (1978).
Kohn, D. B., Current Opinion in Pediatrics 7:56 (1995).
Lebkowski, J. S., et al., Transplantation 53:1011 (1992).
Linse, S., et al., J Biol Chem 266:8050 (1991).
Lonberg, N. and Huszar, D., International Reviews of Immunology 13:65 (1995).
Miltenyi, S., et al., Cytometry 11:231 (1990).
Nilsson, B., et al., EMBO J 4:1075–1080 (1985).
O'Neil, K. T. and DeGrado, W. F., Trends in Biochemical Sciences 15:59 (1990).
Peyrat, M. A., et al., The Immunologist 4:9 (1996).
Posnett, D. N., et al., The Immunologist 4:5 (1996).
Shpall, E. J., et al., Immunomethods 5:197 (1994).
Takio, K., et al., Biochemistry 25:8049 (1986).

What is claimed is:

1. A method for separating target cells from a plurality of cells, said method comprising:

forming a target cell/cell binding reagent/first molecule/second molecule/solid support complex, wherein the cell binding reagent is specific for target cells present within a plurality of cells, wherein the first molecule reversibly binds to the second molecule, wherein one of the first and second molecules is calmodulin, and wherein the other of the first and second molecules is a calmodulin binding peptide;

removing non-target cells of the plurality of cells not attached to the solid support; and reversing the first molecule binding to the second molecule, thereby releasing the target cells as separate cells from the plurality of cells.

2. The method of claim 1 wherein forming a target cell/cell binding reagent/first molecule/second molecule/solid support complex comprises:

reacting a plurality of cells with the cell binding reagent, wherein the cell binding reagent binds to target cells present within the plurality of cells forming target cell/cell binding reagent complexes;

reacting the target cell/cell binding reagent complex with the first molecule to form a target cell/cell binding reagent/first molecule complex; and contacting the target cell/cell binding reagent/first molecule complex with a second molecule and the solid support, wherein the first molecule reversibly binds to the second molecule and the solid support binds to the second molecule, forming the target cell/cell binding reagent/first molecule/second molecule/solid support complex.

3. The method of claim 2 wherein reacting the target cell/cell binding reagent complex with the first molecule to form a target cell/cell binding reagent/first molecule complex comprises linking an anti-cell binding reagent molecule to the first molecule and reacting the linked anti-cell binding reagent molecule with the cell binding reagent, so that the target cell/cell binding reagent/first molecule complex further includes an anti-cell binding reagent molecule linking the cell binding reagent to t first molecule.

4. The method of claim 3 wherein the anti-cell binding reagent molecule is an antibody.

5. The method of claim 3 wherein the anti-cell binding reagent molecule is covalently linked to the first molecule.

6. The method of claim 1 wherein reversing the first molecule binding to the second molecule comprises removing calcium.

7. The method of claim 6 wherein the calcium is removed using a calcium chelator.

8. The method of claim 7 wherein the calcium chelator is EGTA.

9. The method of claim 1 wherein the cell binding reagent is an antibody that specifically binds to a protein antigen specific to the target cell.

10. The method of claim 1 wherein the cell binding reagent contains the first molecule.

11. The method of claim 1 wherein the solid support is a streptavidin solid support and the second molecule is attached to the streptavidin solid support with biotin.

12. The method of claim 1 wherein non-target cells are remove by washing with a buffer.

13. The method of claim 1 wherein the plurality of cells are bone marrow cells for transplantation and the target cells are T cells, tumor cells, or stem progenitor cells.

* * * * *